United States Patent [19]

Felix

[11] 4,425,283

[45] Jan. 10, 1984

[54] METHOD FOR PREPARATION OF N-PHOSPHONOMETHYLGLYCINE

[75] Inventor: Raymond A. Felix, Richmond, Calif.

[73] Assignee: Stauffer Chemical Company, Westport, Conn.

[21] Appl. No.: 442,401

[22] Filed: Nov. 17, 1982

[51] Int. Cl.$^3$ ................................................ C07F 9/38
[52] U.S. Cl. ............................ 260/502.5 F; 564/209
[58] Field of Search ................................. 260/502.5 F

[56] References Cited

U.S. PATENT DOCUMENTS

| | | | |
|---|---|---|---|
| 3,923,877 | 12/1975 | Barton | 260/502.5 F |
| 3,989,772 | 11/1976 | Hendricks et al. | 260/502.5 E |
| 4,053,505 | 10/1977 | Dutra | 260/502.5 F |
| 4,235,809 | 11/1980 | Redmore | 260/502.5 E |

Primary Examiner—J. E. Evans

Attorney, Agent, or Firm—Edwin H. Baker

[57] ABSTRACT

A process for preparing N-phosphonomethylglycine which comprises:

(1) reacting a primary amine with formaldehyde to produce N,N', N''-tris-substituted-hexahydro-s-triazine;

(2) reacting the triazine with an haloacetyl halide, preferably chloroacetyl chloride, to form the N-(substituted)-N-halomethyl acetamide of the haloacetyl halide;

(3) reacting the amide with O,O-di-(substituted)-aminomethylphosphonate to form O,O-di-(substituted)-1-phosphonomethyl-3-(substituted)-1,3-imidazol-4-one; and (4) hydrolyzing the 1,3-imadazol-4-one to yield N-phosphonomethylglycine.

9 Claims, No Drawings

METHOD FOR PREPARATION OF N-PHOSPHONOMETHYLGLYCINE

FIELD OF THE INVENTION

This invention is a new process for preparing N-phosphonomethylglycine.

BACKGROUND OF THE INVENTION

N-Phosphonomethylglycine and certain salts are particularly effective as post-emergence herbicides. The commercial herbicide is sold as a formulation containing the isopropylamine salt of N-phosphonomethylglycine.

N-Phosphonomethylglycine can be made by a number of methods. One such method, as described in U.S. Pat. No. 3,160,632 is to react N-phosphinomethylglycine (glycinemethylenephosphonic acid) with mercuric chloride in water at reflux temperature, and subsequently separating the reaction products. Other methods are phosphonomethylation of glycine and the reaction of ethyl glycinate with formaldehyde and diethylphosphite. The latter method is described in U.S. Pat. No. 3,799,758. In addition, there is a series of patents relating to the preparation of N-phosphonomethylglycine, including U.S. Pat. Nos. 3,868,407, 4,197,254 and 4,199,354.

Close prior art in U.S. Pat. No. 3,923,877, which teaches the reaction of 1,3,5-tricyanomethylhexahydro-1,3,5-triazine with excess disubstituted phosphite to form $(RO)_2P(O)CH_2NHCH_2CN$ (R is hydrocarbyl or substituted hydrocarbyl) which is hydrolyzed to yield N-phosphonomethylglycine.

Because of the commercial importance of N-phosphonomethylglycine and certain salts as herbicides, improved methods of preparing these compounds are valuable.

BRIEF DESCRIPTION OF THE INVENTION

This invention relates to a process for preparing N-phosphonomethylglycine which comprises:

(1) reacting a primary amine with formaldehyde to produce N,N',N''-tris-substituted-hexahydro-s-triazine;

(2) reacting the triazine with an haloacetyl halide, preferably chloroacetyl chloride, to form the N-(substituted)-N-halomethyl acetamide of the haloacetyl halide;

(3) reacting the amide with O,O-di-(substituted)-aminomethylphosphonate to form O,O-di-(substituted)-1-phosphonomethyl-3-(substituted)-1,3-imidazol-4-one; and (4) hydrolyzing the 1,3-imadazol-4-one to yield N-phosphonomethylglycine.

DETAILED DESCRIPTION OF THE INVENTION

The process of this invention may be illustrated by the following reaction scheme:

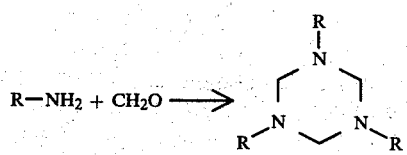 (a)

wherein R is an aromatic or aliphatic group, preferably R is $C_1$–$C_6$ alkyl or $C_3$–$C_6$ alkenyl, more preferably $C_1$–$C_4$ alkyl or $C_3$–$C_4$ alkenyl, most preferably $C_1$–$C_2$ alkyl or $C_3$ alkenyl.

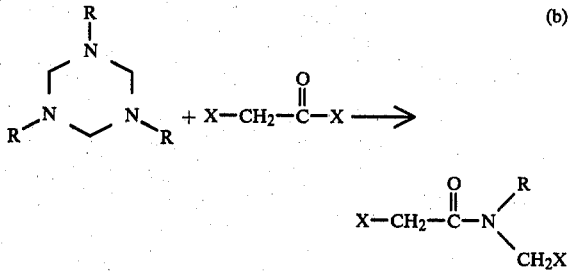 (b)

wherein R is an aliphatic or aromatic group as previously defined, and X is chlorine, bromine, or iodine, most preferably chlorine.

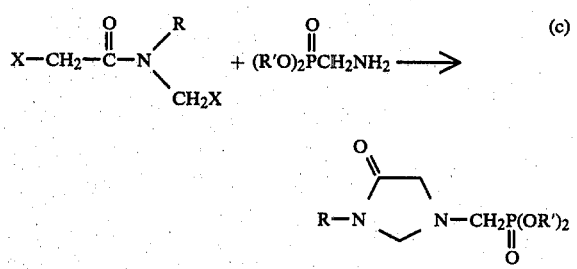 (c)

wherein R and X are as defined as above and R' is an aliphatic or aromatic group, preferably $C_1$–$C_8$ alkyl or $C_3$–$C_6$ alkenyl, more preferably $C_1$–$C_4$ alkyl or $C_3$–$C_4$ alkenyl, most preferably $C_1$–$C_2$ alkyl.

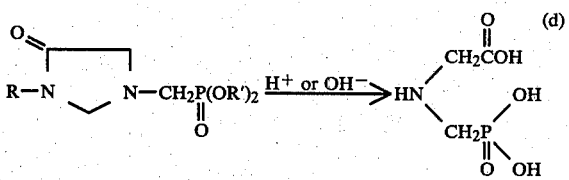 (d)

wherein R and R' are as defined above and H+ is a strong acid such as hydrochloric, hydrobromic, hydriodic, nitric, sulfuric, phosphonic or chloroacetic acid. Preferably H+ is hydrochloric or hydrobromic acid and OH− is a strong base such as sodium hydroxide or potassium hydroxide, preferably in an aqueous, aqueous-alcoholic or alcoholic solution. Preferably, the hydrolysis is run in the presence of a strong acid.

In the above reaction scheme, group R is not directly involved in reaction step (a) between the primary amine and formaldehyde or reaction step (b) between N,N',N''-tris-(substituted)-hexahydro-s-triazine and a haloacetyl halide.

Groups R and R' are not directly involved in reaction step (c) between the N-substituted-N-halomethylacetamide reaction product of step (b) and the O,O-di-substituted-aminomethylphosphonate. Groups R and R' are removed in reaction step (d) when the imidazolone product of reaction step (c) is subjected to hydrolysis. Therefore, the nature of groups R and R' is not critical, although groups which would interfere with reaction steps (b) and (c) are to be avoided. Also, groups that are easily hydrolyzed are preferred for R'.

The group "$C_1$–$C_4$ alkyl" encompasses methyl, ethyl, n-propyl, isopropyl, n-butyl, isobutyl, sec-butyl, and tert-butyl. The group "$C_1$-$C_6$ alkyl" encompasses the same radicals as $C_1$-$C_4$ alkyl plus the 6 pentyls and the 16 hexyls.

The term "aliphatic group" is used in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

Reaction step (a) preferably is run at a temperature between about $-50°$ to about $+150°$ C., more preferably between about $-20°$ to about $+50°$ C. and most preferably between about $0°$ to about $30°$ C. This reaction step can be run at atmospheric, sub-atmospheric or super-atmospheric pressure, preferably at atmospheric pressure. Preferably the reaction is run in a solvent for the amide, such as dichloroethane, dichloromethane, benzene, or ether. One mole of formaldehyde is needed to react with one mole of the primary amine.

Reaction step (b) is preferably run at a temperature between about $-50°$ to about $+130°$ C., more preferably between about $0°$ to about $100°$ C., most preferably between about $40°$ C. and about $80°$ C. This reaction step can be run at atmospheric, sub-atmospheric, or superatmospheric pressure, preferably at atmospheric pressure. Preferably the reaction is run in a solvent for the haloacetyl halide, such as dichloromethane, dichloroethane, toluene, or benzene. Three moles of the haloacetyl halide are needed to react with one mole of the N,N',N"-tris-substituted-hexahydro-s-triazine; furthermore, an excess of the haloacetyl halide can be used to insure complete reaction with the s-triazine. The solvent or any excess haloacetyl halide can be removed to isolate the N-substituted-N-halomethylacetamide of the haloacetyl halide in high yields. However, this amide quickly degrades by hydrolysis and should be kept in an inert atmosphere if isolated.

In reaction step (c), most preferably a mole amount of the N-substituted-N-halomethylacetamide and excess O,O-di-substituted-aminomethylphosphonate are reacted. Less preferably, up to a 10 mole excess can be used. The reaction can be run at a temperature between about $-50°$ C. to about $150°$ C., more preferably between about $-20°$ C. to about $100°$ C., most preferably from about $0°$ to about $30°$ C. Preferably the reaction is run in a solvent, such as acetonitrile, toluene, dichloroethane or dichloromethane. Any solvent used in this reaction step will be removed after completion of reaction step (d), so preferably it is one that can be removed by evaporation.

In reaction step (d), a mole of the imidazolone reaction product from reaction step (c) is hydrolyzed with 4 moles of water. The hydrolysis is run in the presence of a strong acid or base as defined above. Preferably the hydrolysis is acid-catalyzed, preferably with an inorganic acid, and most preferably with hydrochloric or hycrobromic acid. The hydrolysis yields the desired N-phosphonomethylglycine. Preferably at least 2 moles of the acid are used. More preferably, a large excess over the 2 mole amount is used. The preferred hydrochloric or hydrobromic acid can be used in concentrated or aqueous form.

This last reaction step is run at a temperature between about $50°$ to about $200°$ C., preferably between about $80°$ to about $150°$ C. and most preferably between about $100°$ to about $125°$ C. Atmospheric, sub-atmospheric or super-atmospheric pressure can be used. Preferably atmospheric pressure is used during the hydrolysis.

The solid N-phosphonomethylglycine can be recovered by conventional techniques in reaction step (d). Volatile liquid products such as alcohols (methanol) chlorides (methyl chloride), amines, allyl amine, formaldehyde, water, and excess acid can be removed by standard stripping techniques. The desired N-phosphonomethylglycine is recovered in high purity by dissolving it in water, adjusting the pH of the solution to between 1 and 2, allowing it to crystallize from solution and removing it by filtration.

The process of this invention can be better understood by reference to the following specific examples.

EXAMPLE I

Preparation of N,N',N"-Tris-allyl-hexahydro-s-triazine

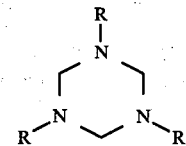

One hundred milliliters (100 ml) (1.34 moles) of allyl amine and 500 ml of toluene were placed in a two liter flask equipped with a mechanical stirrer and an addition funnel. This solution was cooled with an ice bath to about $5°$ C. with vigorous stirring. A solution of 200 ml of water and 136 ml of 37% formaldehyde (1.67 mole) was added slowly. The stirred reaction mixture was then allowed to warm to room temperature. The reaction mixture was stirred for two hours. After separation of the layers, the water layer was washed with 500 ml toluene. The organic layers were dried and stripped under reduced pressure to yield 93.4 g of the desired product N,N',N"-tris-[allyl]-hexahydro-s-triazine. The structure was confirmed by proton nuclear magnetic resonance, mass spectroscopy, and infrared spectroscopy.

EXAMPLE II

Preparation of N-allyl-N-chloromethylchloroacetamide

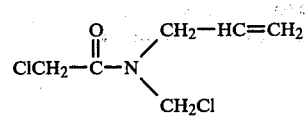

Five ml (0.06 mole) of chloroacetyl chloride and 30 ml of 1,2-dichloroethane were placed in a 200 ml flask equipped with a condenser, an addition funnel, and a mechanical stirrer. This solution was heated to reflux and a solution of 20 ml of 1,2-dichloroethane and 4.14 g (0.02 mole) of N,N',N"-tris-[allyl]-hexahydro-s-triazine was added dropwise with stirring. The reaction mixture was then heated an additional 15 minutes at reflux. The reaction mixture was stripped under reduced pressure to yield 9.8 g of the desired product. The structure was confirmed by proton nuclear magnetic resonance, mass spectroscopy, and infrared spectroscopy.

EXAMPLE III

Preparation of O,O-diethyl-1-phosphonomethyl-3-allyl-1,3-imidazol-4-one

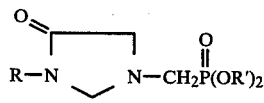

6.3 grams (g) (0.062 mole) of triethylamine in 50 ml of dichloromethane and 5.2 g (0.031 mole) of O,O-diethylaminomethylphosphonate were placed in a 200 ml flask equipped with an addition funnel and a magnetic stirrer. The solution was cooled to about 5° C. in an ice bath, and 5.8 g (0.031 mole) of N-allyl-N-chloromethylchloroacetamide in 25 ml of dichloromethane were added dropwise with vigorous stirring. The reaction mixture was stirred overnight at room temperature. The dichloromethane was stripped under reduced pressure and replaced with 100 ml of diethyl ether. Next, triethylamine hydrochloride was removed by filtration. The ether solution was washed with 100 ml of 1 M sodium hydroxide, and the caustic layer was washed with 100 ml of dichloromethane. Finally, the organic portions were combined and stripped under reduced pressure to yield 3.8 g of the desired product. The structure was confirmed by proton nuclear magnetic resonance, $^{13}C$ nuclear magnetic resonance, mass spectroscopy, and infrared spectroscopy.

EXAMPLE IV

Preparation of N-phosphonomethylglycine

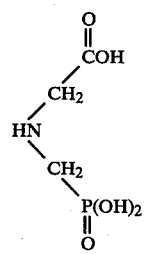

3.5 g of O,O-diethyl-1-phosphonomethyl-3-allyl-1,3-imidazol-4-one and 30 ml of 12 M concentrated hydrochloric acid were placed in a 100 ml flask and heated to reflux for three hours. After stripping the reaction mixture under reduced pressure, the resulting residue was dissolved in 15 ml of water and the pH adjusted to 10 with 50% sodium hydroxide. The solution was then stripped under reduced pressure to remove the allyl amine, yielding 3.3 g of the sodium salt of N-phosphonomethylglycine. The structure was confirmed by proton nuclear magnetic resonance, $^{13}C$ nuclear magnetic resonance, and liquid chromatography techniques.

What is claimed is:
1. A method of preparing N-phosphonomethylglycine comprising
(a) reacting amine of the formula

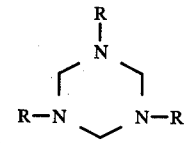

wherein R is an aromatic or aliphatic group with formaldehyde to produce a s-triazine of the formula

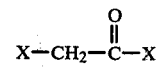

wherein R is as defined;
(b) reacting the triazine formed in step (a) with an acyl halide of the formula

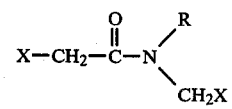

wherein X is chlorine, bromine, or iodine to form an amide compound having the formula

wherein R and X are as defined,
(c) reacting the amide formed in step (b) with O,O-di-substituted-aminomethylphosphonate having the formula $$(R'O)_2 \overset{O}{\underset{\|}{P}} CH_2NH_2$$

wherein R' is an aromatic or aliphatic group to form O,O-di-substituted-1-phosphonomethyl-3-(substituted)-1,3-imidazol-4-one, which has the structural formula

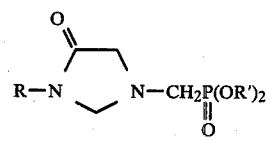

wherein R and R' are as defined; and
(d) hydrolyzing the imidazolone formed in step (c) to yield N-phosphonomethylglycine.
2. The method of claim 1 wherein R is $C_1$-$C_6$ alkyl or $C_3$-$C_6$ alkenyl and X is chlorine.
3. The method of claim 1 wherein R is $C_1$-$C_6$ alkyl or $C_3$-$C_6$ alkenyl, R' is $C_1$-$C_6$ alkyl and X is chlorine.
4. The method of claim 1 wherein R is allyl, R' is $C_1$-$C_4$ alkyl and X is chlorine.
5. The method of claim 1 wherein R is allyl, R' is $C_1$-$C_2$ alkyl, and X is chlorine.
6. The method of claim 1 wherein R is allyl and R' is ethyl and X is chlorine.
7. The method of claim 1 wherein step (b) is run at a temperature between about $-50°$ C. to about 150° C.
8. The method of claim 7 wherein an acid is used in step (d).
9. The method of claim 8 wherein the acid catalyst is hydrochloric or hydrobromic acid.

* * * * *